US006911307B1

(12) United States Patent
Dautel et al.

(10) Patent No.: US 6,911,307 B1
(45) Date of Patent: Jun. 28, 2005

(54) METHOD OF DETECTION IN VITRO OF A TARGET SUBSTANCE IN A SAMPLE COMPRISING THE LABELLING OF SAID SUBSTANCE WITH A REPORTER GENE AND WITH THE SEQUENCES NECESSARY FOR THE EXPRESSION OF SAID REPORTER GENE IN VITRO

(75) Inventors: Sandrine Dautel, Nimes (FR); Cécile Persillon, Nimes (FR); Daniel Dupret, Calvisson (FR); Jean-Michel Masson, Toulouse (FR); Fabrice Lefevre, Nimes (FR)

(73) Assignee: Proteus S.A., Nimes (FR)

( * ) Notice: Subject to any disclaimer, the term of this patent is extended or adjusted under 35 U.S.C. 154(b) by 13 days.

(21) Appl. No.: 09/722,393

(22) Filed: Nov. 28, 2000

Related U.S. Application Data (63) Continuation of application No. PCT/FR99/03061, filed on Dec. 8, 1999.

(30) Foreign Application Priority Data

Dec. 8, 1998 (FR) .............................. 98 15489

(51) Int. Cl.[7] .............................. C12Q 1/68; C12P 19/34

(52) U.S. Cl. .......................... 435/6; 435/69.1; 435/91.2

(58) Field of Search ...................... 435/6, 7.1, 91.1, 435/91.2; 536/22.1, 23.1, 24.3–24.33

(56) References Cited

U.S. PATENT DOCUMENTS

| | | | | |
|---|---|---|---|---|
| 4,800,159 | A | * | 1/1989 | Mullis et al. ............ 435/172.3 |
| 5,602,301 | A | * | 2/1997 | Field .............................. 800/8 |
| 5,952,201 | A | * | 9/1999 | Landegren et al. ........ 435/91.2 |
| 5,972,609 | A | * | 10/1999 | Tinsley et al. ................. 435/6 |

FOREIGN PATENT DOCUMENTS

| | | |
|---|---|---|
| EP | 518557 | 12/1992 |
| GB | 2276621 | 10/1994 |
| WO | WO 92/07949 | 5/1992 |
| WO | WO 94/03630 | 2/1994 |
| WO | WO 94/05812 | 3/1994 |
| WO | WO 94/06928 | 3/1994 |
| WO | WO 96/01327 | 1/1996 |
| WO | WO 96/08580 | 3/1996 |
| WO | WO 97/19193 | 5/1997 |
| WO | WO 98/11249 | 3/1998 |
| WO | WO 98/27225 | 6/1998 |

OTHER PUBLICATIONS

Watson J.D. et al Recombinant DNA 2nd edition, 1992, WH Freeman & Company p. 155.*
Gibco BRRL products & reference Guide pp. 15–6, 19–4, 19–5 1997.*
Amersham Catalogue pp. 116 1998.*
Ohuchi et al Nucleic Acids Research vol. 26 No. 19 pp. 4339–4346 1998.*
Sarkar et al Biotechniques vol. 8 No. 4 pp. 404–407 1990.*
Cassata, G. et al., "Rapid Expression Screening of Caenorhabditis Elegans Homeobox Open Reading Frames Using a Two–Step Polymerase Chain Reaction Promoter–*gfp* Reporter Construction Technique", *Gene*, vol. 212; pp. 127–135 (1998).

(Continued)

Primary Examiner—Kenneth R. Horlick
(74) Attorney, Agent, or Firm—Hunton & Williams LLP (57) ABSTRACT

The present invention relates to a method of detection in vitro of a target substance in a sample. The sample can comprise, among other things, a nucleic sequence or more generally any type of substance. In particular, the present invention provides a method of detection comprising (i) specificly labeling a substance with a reporter gene and any sequences necessary for the in vitro expression of the reporter gene; (ii) in vitro transcription and translation of the reporter gene; and (iii) in vitro detection of a reporter protein coded by the reporter gene.

31 Claims, 6 Drawing Sheets

OTHER PUBLICATIONS

Hanes, J. et al., "In Vitro Selection and Evolution of Functional Proteins by Using Ribosome Display", *Proc. Natl. Acad. Sci.*, vol. 94, pp. 4937–4942 (1997).

Resto et al., "Amplification of Protein Expression in a Cell Free System", *Nucleic Acids Research*, vol. 20, No. 22, pp. 5979–5983 (1992).

Sun, Y. et al., "Comparison of Peptide Enzyme–Linked Immunosorbent Assay and Radioimmunoprecipitation Assay with In Vitro–Translated Proteins for Detection of Serum Antibodies to Human Papillomavirus Type 16 E6 and E7 Proteins", *Journal of Clinical Microbiology*, vol. 32. No.9, pp. 2216–2220 (1994).

* cited by examiner

SEQUENCE LISTING

<160> NUMBER OF SEQ ID NOS: 9

<210> SEQ ID NO 1
<211> LENGTH: 35
<212> TYPE: DNA
<213> ORGANISM: Artificial Sequence
<220> FEATURE:
<223> OTHER INFORMATION: MICRO1

<400> SEQUENCE: 1
tatgtgcgca caatgtcata cagtagaata ataac                35

<210> SEQ ID NO 2
<211> LENGTH: 37
<212> TYPE: DNA
<213> ORGANISM: Artificial Sequence
<220> FEATURE:
<223> OTHER INFORMATION: MICRO2

<400> SEQUENCE: 2
tcgagttatt attctactgt atgacattgt gcgcaca                37

<210> SEQ ID NO 3
<211> LENGTH: 37
<212> TYPE: DNA
<213> ORGANISM: Artificial Sequence
<220> FEATURE:

```
<223> OTHER INFORMATION: MICRO2 (3' to 5' orientation)

<400> SEQUENCE: 3
acacgcgtgt tacagtatgt catcttatta ttgagct                                37

<210> SEQ ID NO 4
<211> LENGTH: 27
<212> TYPE: DNA
<213> ORGANISM: Artificial Sequence
<220> FEATURE:
<223> OTHER INFORMATION: pET5'

<400> SEQUENCE: 4
agatctcgat cccgcgaaat taatacg                                           27

<210> SEQ ID NO 5
<211> LENGTH: 26
<212> TYPE: DNA
<213> ORGANISM: Artificial Sequence
<220> FEATURE:
<223> OTHER INFORMATION: pET3'

<400> SEQUENCE: 5
caaaaaaccc ctcaagaccc gtttag                                            26

<210> SEQ ID NO 6
<211> LENGTH: 158
<212> TYPE: DNA
<213> ORGANISM: Artificial Sequence
<220> FEATURE:
<223> OTHER INFORMATION: Padlock Probe

<400> SEQUENCE: 6
ttcagcagga ttccccacag caaaattatt tctagaggga aaccgttgtg gtctccctat       60
agtgagtcgt attaattttt attattctac tgtatgacat tgtgcgcaca tatgtatatc      120
tccttcttaa agttaaaccc gtcgatcata aggcttgg                              158

<210> SEQ ID NO 7
<211> LENGTH: 40
<212> TYPE: DNA
<213> ORGANISM: Artificial Sequence
<220> FEATURE:
<223> OTHER INFORMATION: Padlock probe recognition sequence

<400> SEQUENCE: 7
ctgtggggaa tcctgctgaa ccaagcctta tgatcgacgg                             40

<210> SEQ ID NO 8
<211> LENGTH: 24
<212> TYPE: DNA
<213> ORGANISM: Artificial Sequence
<220> FEATURE:
<223> OTHER INFORMATION: PADRCMP8

<400> SEQUENCE: 8
tttaacttta agaaggagat atac                                              24

<210> SEQ ID NO 9
<211> LENGTH: 20
<212> TYPE: DNA
<213> ORGANISM: Artificial Sequence
```

-continued

```
<220> FEATURE:
<223> OTHER INFORMATION: PADPCR5'

<400> SEQUENCE: 9
ttcagcagga ttcccacag                                                    20
```

METHOD OF DETECTION IN VITRO OF A TARGET SUBSTANCE IN A SAMPLE COMPRISING THE LABELLING OF SAID SUBSTANCE WITH A REPORTER GENE AND WITH THE SEQUENCES NECESSARY FOR THE EXPRESSION OF SAID REPORTER GENE IN VITRO

CROSS-REFERENCE TO RELATED APPLICATIONS

This application is a continuation of PCT/FR99/03061, filed Dec. 8, 1999, which claims priority to French Patent Application No. FR98/15489, filed Aug. 12, 1998.

BACKGROUND OF THE INVENTION

The present invention relates to a method of detection in vitro of a target substance, notably a nucleic sequence but more generally any type of substance, in a sample. The search for target substances, notably for nucleic acid sequences, represents a primary object in numerous research laboratories implicated in numerous fields of activity, and principally in the medical or agribusiness fields. In these fields, the search for target sequences is directed for example to:

The diagnosis of a virus at the origin of diseases, such as AIDS (HIV) or hepatitis B (HBV).

The specific diagnosis of diseases of bacterial origin, such as tuberculosis or leprosy.

The diagnosis of mutations at the origin of genetic diseases or of cellular cancers.

The diagnosis of bacterial contamination in an agribusiness food chain.

The search for microorganisms implicated in the biological corrosion of pipes or of containers used in industrial processes.

The major difficulty of the diagnosis methods used in the prior art resides in the specificity, the sensitivity, the speed and the reproducibility of the detection test used. These difficulties generally come from the nature of the labeling used. In effect, the nature of the labeling of a substance is the decisive factor in any subsequent detection permitting the following or the quantifying of said substance. Regardless of whether it concerns a human, animal or vegetable diagnosis, in agribusiness, therapy, pharmacology, research, in varied industrial processes etc., it is necessary to detect, to follow and to specifically qualify one or several target substances. In order for this detection to be optimal, it is necessary to set up high performance and sensitive labeling techniques One of the specific techniques for labeling nucleic acids uses PCR amplification. The labeling of primers which can be used in PCR can be carried out in two ways, either by labeling of the primers, preferably at their 5' ends or by internal marking of the amplified fragment.

The first type of labeling has the disadvantage of having a low specific activity and consequently, limits the sensitivity of the later revelation. It is possible to fix a radioactive phosphate ($^{32}P$) at the 5'end of the primers. There will be one ($^{32}P$) per primer. If biotin or a fluorochrome is fixed, it is possible to have at the most 3 to 4 labels per primer molecule.

If the radioactive nucleotides are incorporated in the amplicon, the specific activity is certainly more important, but it is necessary to manipulate radioactivity more. The current tendency is to replace the isotopic labeling methods with cold labeling (fluorophore, digoxigenine, biotin).

The fluorophores are sensitive to environmental changes: variations in the experimental conditions (pH, presence of oxidizing elements, etc . . . ) can displace the emission wavelength. In addition, the phenomena of fluorescence extinction (or quenching) have largely been described. The incorporation of nucleotides labeled with a fluorophore or with digoxigenine or with biotin by polymerases is of low effectiveness because these nucleotides have a strong steric hindrance which disturbs the PCR polymerization reaction.

The radioactive labeling of proteins can be carried out by using amino acids labeled with an isotope, which implicates the manipulation of radioactivity. The labeling of proteins by an antigen/antibody reaction may for its part not be so sensitive.

SUMMARY OF THE INVENTION

The object of the present invention is precisely to offer a method of, detection of sensitive target substances not giving rise to the disadvantages hereinabove.

This object is achieved thanks to a method of detection of a target substance in a sample, characterized in that it comprises the following steps:

a) the specific labeling of said substance by a reporter gene and by sequences necessary for the expression of said reporter gene in vitro, b) The transcription and translation in vitro of said reporter gene, c) The detection in vitro of the reporter protein coded by said reporter gene.

The method of the invention is therefore based on a labeling consisting of combining with the target substance a DNA molecule constituting a reporter gene which can be expressed in vitro. The labeling therefore consists of combining with the target substance, a reporter gene placed under the control of sequences necessary for its expression.

The in vitro transcription promoters which can be used within the scope of the invention can notably correspond to the promoters of the phages T7, SP6, Qα or λ.

At step (b), the protein encoded by the reporter gene is obtained in a way so as to specifically reveal the target substance.

The revelation of the labeling which is the object of the process of the invention is sensitive because it makes use of amplification steps during steps of transcription (step b), of translation (step b) and of detection (step c). This amplification can correspond for example to a factor of 500 for the transcription (Pokrovkaya and Gurevich, Analytical Biochemistry 220, 420–423 (1994).

The method of the invention is also specific in the test of detection of the protein at step (c).

Moreover the method of the invention can go through after the transcription step a step of amplification of the transcripts by all techniques known to a person skilled in the art such as 3 SR, NASBA (nucleic Acid Sequence-based amplification), TMA (Transcription Mediated Amplification).

In the case where the target substance corresponds to a nucleic acid molecule, the amplification of the signal of revelation can begin during step (a) of the method of the invention. A set of primers or of particular probes is used so as to specifically amplify a sequence and to combine in the presence of a specific oligonucleotide sequence a reporter gene which can be expressed in vitro. The reporter gene is expressed only if the target gene is present and amplified. As indicated above, amplification of the reporter gene or of the target gene is understood as PCR type reactions (polymerase chain reaction), NASBA (nucleic acid sequence-based amplification), SDA (strand displacement amplification), bDNA (branched DNA signal amplification), rolling circle, techniques derived from PCR (nested PCR, multiplex PCR).

The method of the invention moreover is fast and reproducible, because all of the reactions are carried out in vitro, which permits standardization of the detection. The method of the invention permits carrying out qualitative and quantitative detections.

The method of the invention is notable in that it can be applied to any type of substance. However, the invention is more particularly applied to chemical or biological substances, such as antibodies, fragments of antibodies, nucleotide fragments, genes, cellular receptors, peptides, proteins, amino acids, glycopeptides, lipids, glycolipids, sugars, polysaccharides, etc . . . In a particular application, the target substance can be the reporter gene itself.

Labeled target substance is understood as any substance directly or indirectly associated with a reporter gene which can be expressed in vitro.

The reporter gene is a gene which can be transcribed and translated in vitro in the presence of sequences which regulate its expression. The protein that the reporter gene codes for can be detected at step (c) by any technique known to a person skilled in the art. By way of example, the reporter gene can be the gene of the protein GFP (Green Fluorescent Protein) or that of the beta-lactamase (TEM-1). In the case of the GFP, it is the fluorescent emission which is measured. In the case of the beta-lactamase, it is the activity of this enzyme which is measured by incubating a fraction of the translation reaction in a buffer containing nitrocephine. Nitrocephine is a chromogenic beta-lactamine which has the property of changing color from yellow to red when it is hydrolyzed by a beta-lactamase. Any other reporter gene can be contemplated in the process of the invention, such as beta-galactosidase, beta-glucuronidase, luciferase, peroxidase or a microperoxidase, etc . . .

The reporter gene advantageously encodes for an enzyme. The specificity of the labeling of the target substance at step (a) of the method of the invention can be carried out by any direct or indirect method known to a person skilled in the art.

For the direct method, it is understood that the target substance is directly combined with the gene and with the elements necessary for the expression of said reporter gene in vitro. It relates for example to the case described hereinafter of a recombinant nucleic acid molecule where the target substance is a nucleic sequence included in said recombinant nucleic acid molecule equally including the reporter gene and the sequences necessary for its in vitro expression.

For the indirect method, it is understood that the target substance is combined with a reporter gene and with the sequences necessary for its expression in vitro, by the intermediary of a specific ligand of the of the target substance. This ligand is combined with the reporter gene and with the elements necessary for its expression in vitro. It is therefore the contacting of this ligand with the target substance which permits the carrying out of the specific labeling of the target substance. It relates for example to an antibody labeled by the reporter gene and the sequences necessary for its expression in vitro which is capable of specifically recognizing a target substance composed of an antigen. A target/ligand couple substance is understood as for example: an antigen/antibody, a nucleic sequence/a nucleic sequence, a probe, a receptor/a receptor ligand, etc . . .

In the indirect embodiment, the method of the invention consists at step (a) of contacting the sample liable to contain the target substance with a ligand specific for this target substance, said ligand being labeled by a reporter gene and by the sequences necessary for the expression of said reporter gene in vitro. The remainder of the method includes as previously the steps (b) and (c).

The labeling of the specific ligand of the target substance can be as previously a direct or indirect labeling.

According to the indirect method of the invention, the combination of the reporter gene and a target sequence corresponding to a protein allows several embodiments. In effect, the bonding of a nucleic acid molecule composed of a reporter gene and of the sequences necessary for its expression in vitro, on a protein can be carried out by techniques known to a person skilled in the art making use of bonding compounds such as:

streptavidine/biotin (Kipriyanov et al., (1995). Hum Antibodies Hybridomas 6 (3), 93–101)

a peptide corresponding to polylysine (Avrameas et al., (1998). PNAS 95 (10), 5601–6; Curiel et al., (1992). Hum Gen Ther 3 (2), 147–54; Wu et al., (1991). J Biol Chem 266 (22), 14338–42; Kwoh et al., (1999). Biochim Biophys Acta 1444 (2), 171–90; Wu et al., (1994). J Biol Chem 269 (15), 11542–6 the p-azido-tetrafluoro-benzyl (Ciolina et all, (1999). Bioconjug Chem 10 (1), 49–55).

The triple helices of DNA (Neves et al., (1999). FEBS Lett 453 (1–2), 41–5.

DETAILED DESCRIPTION OF THE INVENTION

A preferred form of implementation of the process of the invention relates to nucleic detection of a sequence targets, advantageously by the direct method.

The method of the invention offers the advantage of being able to specifically detect a target sequence in a sample to be analyzed and to later work directly on this target sequence.

The method of the invention is also notable in that it is quite particularly adapted to the detection of target nucleic acid sequences coding for a peptide or a protein not having identifiable activity in vitro.

According to a first preferred aspect of carrying out the method of the invention the preparation of the nucleic acid molecule of step (a) is carried out by in vitro amplification of the target nucleic acid sequence.

It relates to an amplification by PCR or by techniques derived from PCR of the RT-PCR, nested PCR, multiplex PCR type or techniques different from PCR: NASBA (nucleic acid sequence-based amplification) or rolling circle or others.

In an aspect of carrying out the method of the invention, hereinafter designated "universal," the first step (a) of the method is based on the carrying out of an amplification reaction of the target sequence, if it is understood that it is present in the analyzed sample, with the aid of two primers designated sense and anti-sense as defined below:

a sense primer including at least one part homologous to the regions 5' of the target sequence, an anti-sense primer comprising at least one part homologous to the region 3' of the target sequence.

said primers permitting after amplification of the target nucleic acid sequence, and after step (b), the expression of the reporter gene.

The invention therefore also relates to a set of primers capable of being used at step (a) of a method according to the invention characterized in that it comprises:

a sense primer comprising at least one part homologous to the region 5' of the target sequence, an anti-sense primer, comprising at least one part homologous to the region 3' of the target sequence, said primers permitting after amplification of the target nucleic acid sequence, and after step (b), the expression of a reporter gene.

Figure 1:
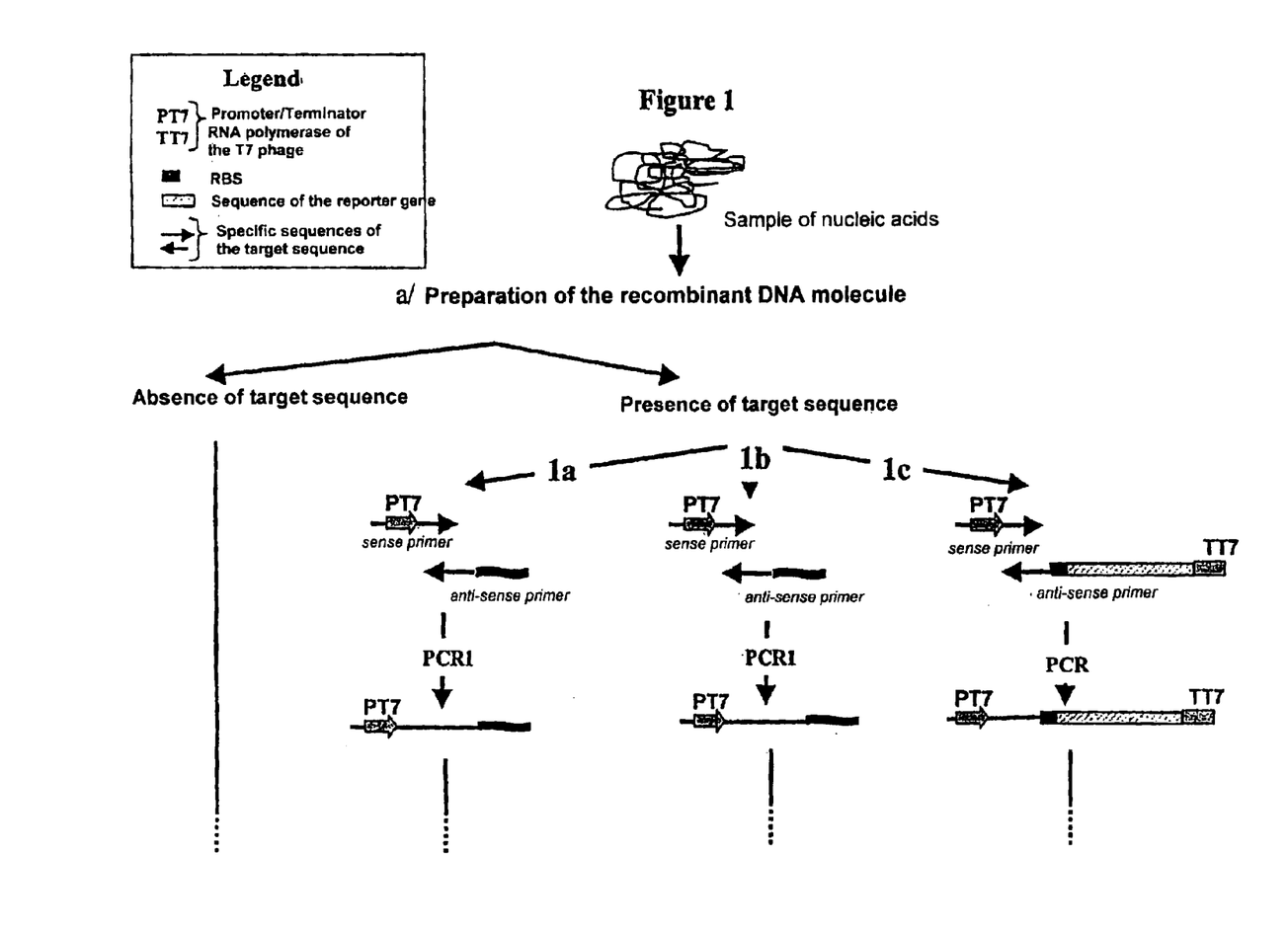
FIG. 1 shows one embodiment of the invention involving amplication of a target sequence with a sense primer and an anti-sense primer.

In a first specific embodiment of the universal method of the invention, step (a) includes the three following reactions (FIG. 1a):

a') the amplification of the target sequence with a pair of primers wherein the sense primer possess an RNA polymerase promoter and the anti-sense primer possess a 5' region homologous at the beginning of the sequence of the reporter gene, and a'') the contacting of the amplification products of the preceding reaction with the reporter gene optionally possessing an RNA polymerase terminator for its transcription, a ribosome binding site for its translation, so as to hybridize said amplification products with said reporter gene, then a''') the amplification of the products of step (a'') with a pair of primers, wherein the sense primer is similar to that of step (a') and the anti-sense primer includes a part homologous to a region downstream of the reporter gene.

In this embodiment, the PCR reaction mixture contains the sample DNA, two sense and anti-sense primers, the reporter sequence and a third primer homologous to a region downstream of the reporter gene. The first amplification of step (a') and the second amplification of step (a''') can be carried out simultaneously or not.

As shown in FIG. 1a attached, the first cycles of the PCR1 reaction permit the amplification of the target sequence. Once this sequence is present in a sufficient quantity in the reaction medium, it serves as a mega-primer and comes to be hybridized to the reporter sequence, which is thus amplified thanks to the third primer.

In a second embodiment of the universal method of the invention, step (a) includes the two following reactions (FIG. 1b):

a') the amplification of the target sequence with a pair of primers wherein the sense primer possess an RNA polymerase promoter and the anti-sense primer possess a 5' region homologous to the beginning of the sequence of the reporter gene, and a'') the amplification of the products of step (a') with a pair of primers wherein the sense primer is identical to that of step (a') and the anti-sense primer is a mega-primer composed of the reporter gene optionally possessing an RNA polymerase terminator for its transcription, a ribosome binding site for its translation.

In this embodiment, the anti-sense primer possess a 5' region homologous to the beginning of the reporter sequence, which possess, as previously, all the information for its own translation. As indicated at FIG. 1b attached, the PCR reaction mixture contains the sample DNA, two sense and anti-sense primers and a mega-primer corresponding to the reporter sequence. The anti-sense primer is present in a less large quantity than the sense primer. The first cycles of the PCR1 reaction permit the amplification of the target sequence. Once this sequence is present in sufficient quantity in the reaction mixture, it is amplified (PCR2) with the aid of the PCR1 sense primer and the mega-primer.

In a third embodiment of the universal method of the invention (FIG. 1c), step (a) includes the amplification reaction of the target sequence with a pair of primers wherein the sense primer possesses an RNA polymerase promoter and the anti-sense primer possesses a 5' region including a sequence coding for a ribosome binding site, a reporter gene and optionally a transcription terminator.

In this embodiment represented in FIG. 1c attached, the anti-sense primer possesses a 3' region specific to the target sequence and a 5' region corresponding to a sequence coding for a ribosome binding site, a reporter gene and optionally a transcription terminator. The PCR reaction mixture contains the sample DNA, two sense and anti-sense primers.

The invention equally relates to a labeling mixture for amplification for the carrying out of the embodiments described above. Such a mixture includes, the reactants necessary for carrying out the amplification cycles, and therefore more particularly, the four deoxynucleotide triphosphates, the salts and the reactants which assure the optimal DNA polymerase activity, as well as the different types of primers described above.

A labeling mixture for amplification more particularly adapted for the carrying out of step (a) of the first embodiment of the universal method according to the invention includes:

a pair of primers wherein the sense primer possesses an RNA polymerase promoter and the anti-sense primer possesses a 5' region homologous at the beginning of the sequence of the reporter gene.

The reporter gene optionally possessing an RNA polymerase terminator for its transcription, and a ribosome binding site for its translation, and A third primer homologous to a region downstream of the reporter gene.

A labeling mixture for amplification more particularly adapted to the carrying out of step (a) of the second embodiment of the universal method according to the invention includes:

a pair of primers wherein the sense primer possesses an RNA polymerase promoter and the anti-sense promoter possesses a 5' region homologous to the beginning of the sequence of the reporter gene, and a mega-primer composed of the reporter gene optionally possessing an RNA polymerase terminator for its transcription and a ribosome binding site for its translation.

A labeling mixture for amplification more particularly adapted to the carrying out of step (a) of the third embodiment of the universal method according to the invention comprises a pair of primers wherein the sense primer possesses an RNA polymerase promoter and the anti-sense primer possesses a 5' region comprising a sequence coding for a ribosome binding site, a reporter gene and optionally a transcription terminator.

The invention therefore equally has for an object a kit for the detection of a nucleic acid target sequence in a sample in accordance with the universal method previously described.

A kit for the detection of a nucleic acid target sequence in a sample according to the invention includes a set of primers defined above, a mixture necessary for the amplification, the triphosphate nucleotides, a DNA dependent RNA polymerase, a DNA dependent DNA polymerase, a cellular translation extract, the mixtures necessary for transcription, translation and optionally revelation of the reporter molecule, and optionally one or several substances permitting revelation of the activity of the reporter molecule.

A particular example of a kit according to the invention further comprises, one of the amplification mixtures above, a DNA dependent DNA polymerase, the triphosphate nucleotides and the triphosphate deoxynucleotides, a DNA dependent RNA polymerase, a cellular translation extract, the mixtures necessary for amplification, transcription and translation and optionally one or several substances permitting revelation of the activity of the reporter molecule.

The method of the invention, at the level of step (a), can equally be used based on the properties of the probes called "Padlock (WO 97/19193 and bibliographic references 1, 2, 3, and 4). This embodiment is more particularly adapted to the detection of target sequences possessing a point mutation.

The detection of target sequences using the "Padlock" probes therefore constitutes an alternative to the previously described embodiments of the so-called universal method of the invention.

The invention therefore equally relates to a method for in vitro detection of a target nucleic acid sequence in a sample characterized in that the preparation of the nucleic acid molecule of step (a) is carried out by hybridization and ligation of a Padlock probe with the target sequence if it is present in the sample.

Said probe is composed at its 3' and 5' ends of segments separated by the complementary sequence of a reporter gene which possesses the complementary sequences of a promoter and possibly of an RNA polymerase terminator for its transcription, and the complementary sequence of a ribosome binding site for its in vitro translation, the sequences of said 3' and 5' segments of the Padlock probe being complementary of the sought-after target sequence in a manner so as to form with it a joined hybrid, and the 5' end of the probe possessing a phosphate group so as to permit the circularization of the probe under the action of a ligase. There will preferably be used a nick-sealing ligase. In this way, in the absence of target sequence, the probe cannot be circularized.

Said probe can likewise be composed at its 5' and 3' ends of segments separated from 5' to 3' by the sequence of an RNA polymerase promoter, a ribosome binding site and the sequence of a reporter gene optionally with an RNA polymerase terminator.

The segments 3' and 5' of the Padlock probe are therefore defined by their being hybridized in complementary and joined manner to a target sequence.

As previously indicated, the method of the invention based on the use of a padlock probe can advantageously be used for the in vitro detection of a target nucleic acid sequence having a mutation. In this case, the preparation of the nucleic acid molecule of step (a) is carried out by hybridization of a Padlock type probe with the target sequence if it is present, said probe corresponding to one of the two probes previously described with the following in particular: the sequences of said segments 3' and 5' of the Padlock probe are complementary to the sought-after target sequence in a matter so as to form with it a hybrid where the critical nucleotide liable to be mutated, is found at their junction when they are hybridized to the target sequence.

Figure 2:
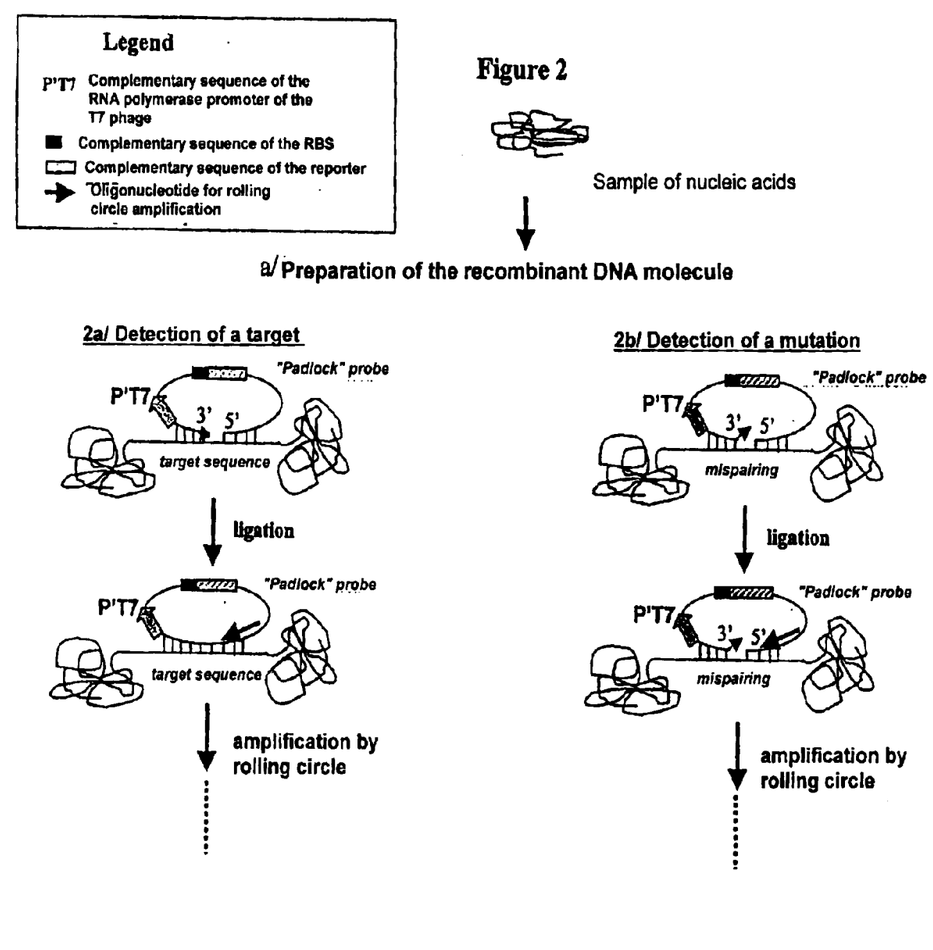
FIG. 2 shows one embodiment of the invention involving use of a Padlock probe.

Thus, when the method of the invention is applied to the demonstration of the presence of a mutation at the level of a target sequence, as shown in FIG. 2b, the segments 3' and 5' of the "Padlock" probe are defined in such a manner that the critical nucleotide, liable to be mutated, is found at their junction when they are hybridized to the target sequence. In case of mispairing, the ligase will not be able to bond the two ends and the circularization of the probe will not be able to occur.

The invention therefore also relates to a Padlock probe capable of being used in the above method, characterized in that the sequences of said segments 3' and 5' of the Padlock probe are complementary to a target sequence having a nucleotide capable of being mutated in a manner so as to form with it a hybrid where said nucleotide is found at their junction when they are hybridized to the target sequence.

Advantageously, in the method of the invention based on the use of a padlock probe, after circularization, the probe is used as a matrix for its replication by a rolling circle. The replication by a rolling circle is carried out with the aid of a primer complementary to the padlock probe in order to initiate the replication by DNA polymerase, in such a way as to produce a DNA matrix possessing a linking of reporter genes with all the signals necessary for its in vitro expression (either, from 5' to 3', a repetition of the following element (RNA polymerase promoter, ribosome binding site, reporter gene and optionally RNA polymerase terminator), or the complement of that sequence according to the probe chosen then the complementary strand of that DNA matrix is synthesized starting from a second oligonucleotide primer in such a way to make this matrix double stranded.

This preparation step increases the sensitivity of the detection thanks to numerous copies of the reporter produced starting from a single target molecule A particularly preferred embodiment of the method of the invention based on the padlock probes consists of carrying out directly at step b) the transcription of the reporter gene on the Padlock probe after its circularization and the synthesis of the complementary strand with the aid of a primer complementary to the padlock probe complementary to the target.

This embodiment includes the preparation at step (a) of a padlock probe corresponding to those previously described permitting either the detection of a nucleic acid sequence or the detection of a mutation on a nucleic acid sequence. This padlock probe is created in such a fashion that the direct transcription of the reporter gene by RNA polymerase can only take place if the padlock probe was previously circularized following its hybridization on the target nucleotide sequence. In this case, there is not any rolling circle amplification, but only the synthesis of the complementary strand of the padlock probe with the aid of a primer complementary to the padlock probe complementary to the target, and optionally ligation then direct transcription of the reporter gene of the padlock probe by RNA polymerase.

The invention relates as well to kits for the implementation of the method of the invention using a padlock probe.

Such a kit is characterized in that it includes a probe as described previously, a DNA dependent DNA polymerase, a nick-sealing ligase, the triphosphate nucleotides and the triphosphate deoxynucleotides, a primer for initiating the replication, a primer permitting the synthesis of the second strand of DNA, a DNA dependent RNA polymerase, the mixtures necessary for the ligation, replication, transcription, translation and the revelation of the reporter molecule.

A first example of a kit according to the invention more particularly includes:

One of two probes of Padlock type previously described. The sequences of said segments 3' and 5' of the Padlock probe are complementary to the sought-after target sequence in such a manner as to form with it a jointed hybrid, and the 5' end of the probe possesses a phosphate group in such a way as to permit the circularization of the probe under the action of a ligase.

A DNA dependent DNA polymerase, a nick-sealing ligase, the triphosphate nucleotides and the triphosphate deoxynucleotides, a primer for initiating the rolling circle replication, a primer permitting the synthesis of the second strand of the DNA matrix generated by a rolling circle, a DNA dependent RNA polymerase, the mixtures necessary for the ligation, labeling, replication, transcription, translation and revelation of the reporter molecule.

A second example of a kit according to the invention more particularly comprises:

one of two Padlock type probes previously described. The sequences of said segments 3' and 5' of the Padlock probe are complementary to the sought-after target sequence in such a manner as to form with it a hybrid where the critical nucleotide liable to be mutated, is found at their junction when they are hybridized to the target sequence, and the 5' end of the probe possesses a phosphate group in a fashion so as to permit the circularization of the probe under the action of a ligase.

a DNA dependent DNA polymerase, a nick sealing ligase, the triphosphate deoxynucleotides, the triphosphate nucleotides, a primer for initiating the rolling circle replication, a primer permitting the synthesis of the second strand of the DNA matrix generated by a rolling circle, a DNA dependent RNA polymerase, the mixtures necessary for the ligation, for the labeling, for the replication, for the transcription, for the translation and for the revelation of the reporter molecule.

A third type of kit for the particularly preferred embodiment of the above method of the invention using a padlock probe comprises:

one of the Padlock type probes described previously permitting either the detection of a nucleic acid sequence or the detection of a mutation on a nucleic acid sequence.

A DNA dependent DNA polymerase, a ligase, the triphosphate deoxynucleotides, the triphosphate nucleotides, a primer for synthesizing the complementary strand of the circularized padlock probe, a DNA dependent DNA polymerase, the mixtures necessary for ligation, labeling, replication of the DNA, transcription, translation, and optionally revelation of the reporter molecule, and optionally one or several substances permitting revelation of the activity of the reporter molecule.

The method of the invention can equally be implemented in the scope of an isothermic amplification also designated CIA for "Continuous Thermic Amplification" of the type described in international patent application PCT No. WO96/01327.

In this method of carrying out the method of the invention, the sought-after target nucleic acid sequence is isolated from a nucleic acid sample at step (a) by specific isothermic amplification with the aid of a DNA dependent DNA polymerase and of two specific primers of the target sequence, wherein at least one is composed of a 3' part which can be specifically hybridized to the target sequence and of a 5' part composed of at least one reversed repeated sequence in order to form at an suitable temperature a structure called a "hairpin." The fusion temperature of the double-stranded hairpin structure is preferably less than or equal to the fusion temperature of the part of the primer specifically hybridizing with the target sequence. The difference between the two fusion temperatures is for example about 10° C. Moreover, one of the primers carries the sequence of a DNA dependent RNA polymerase transcription promoter, such as the RNA polymerase promoter of the phage T7 and the other primer carries a reporter gene possessing at its 5' end a ribosome binding site.

In this embodiment of the invention, a gene coding for a microperoxidase can be cited more particularly as a reporter gene.

According to an advantageous embodiment, the two primers possess a reversed repeated sequence in order to form at a suitable temperature a hairpin structure. The reversed repeated sequences of the two primers can be identical or different. It is preferred that they be different in order to avoid hybridization between them.

Figure 3:
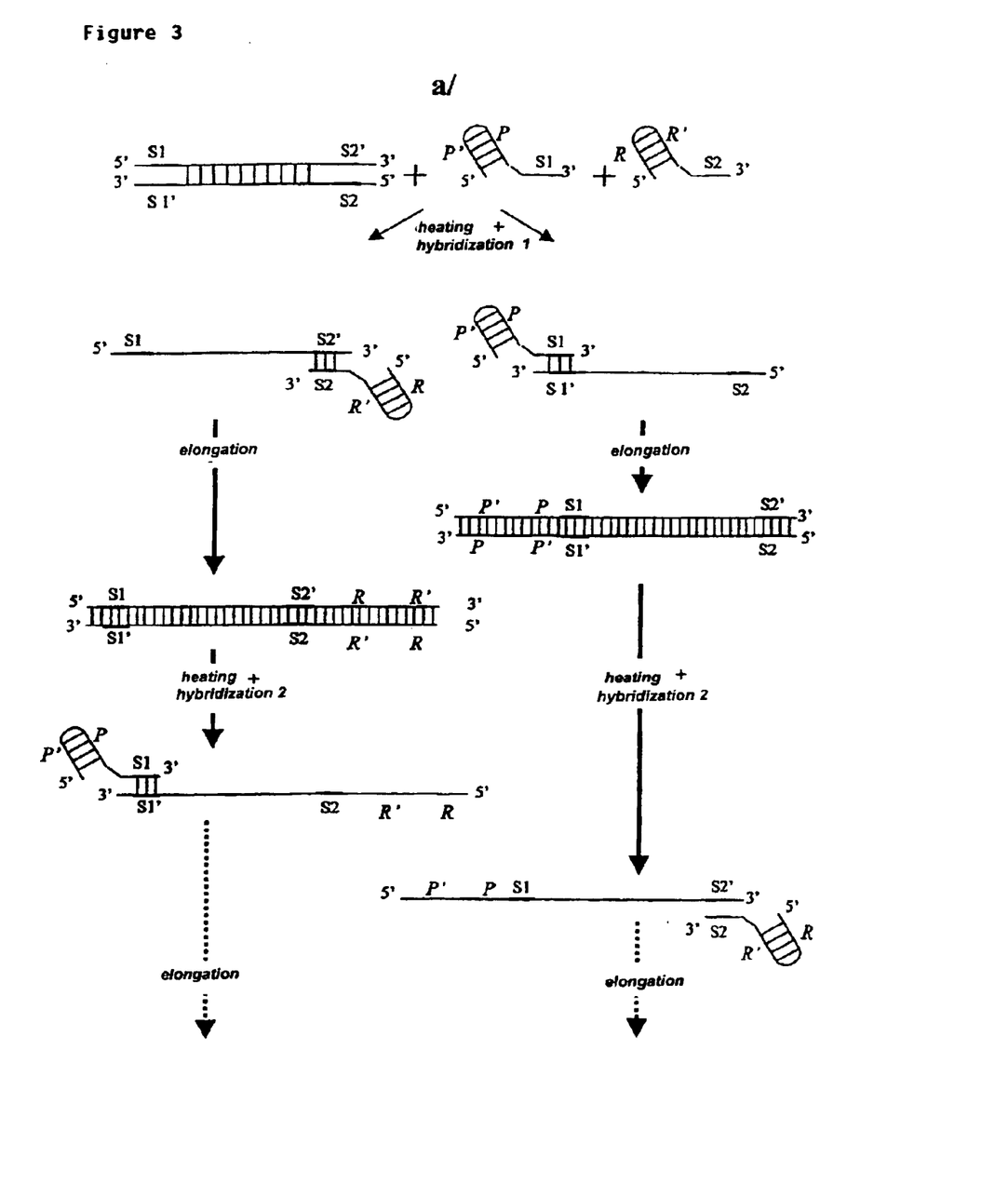
FIG. 3 shows one embodiment of the invention involving isothermic amplification.

A schematic representation of the method of the invention based on an isothermic amplification is given at FIG. 3 attached. Among the different pairs of primers which can be used in this embodiment of the method of the invention, the pair of preferred primers, designated A, can be more particularly cited as follows:

a sense primer composed, from 5' to 3', of a the reversed complementary sequence of an RNA polymerase promoter, of the sequence of said RNA polymerase promoter, and of a specific sequence capable of being hybridized upstream of the target sequence, an anti-sense primer composed, from 5' to 3', of a ribosome binding site, of a reporter gene, of the reversed complementary sequence of said reporter gene and of said ribosome binding site, and of a specific sequence capable of being hybridized downstream from the target sequence, at least one of said primers optionally including a restriction site.

The invention also relates to a set of primers which can be used in the above method, characterized in that it comprises:

a sense primer including at least one part homologous at the 5' region to the target sequence.

An anti-sense primer, comprising at least one part homologous at the 3' region to the target sequence.

said primers permitting after amplification of the target nucleic acid sequence and after the step (b) the expression of a reporter gene, and at least one of said primers comprising at 5' a repeated reversed sequence.

The isothermic amplification is carried out with the following reaction medium:

the matrix nucleic acid molecule possessing the target sequence, the four triphosphate deoxynucleotides, the salts and reactants assuring an optimal activity of the DNA polymerase, a DNA dependent DNA polymerase, a pair of primers specific to the target sequence to amplify and comprising the repeated reversed sequences defined above.

The DNA dependent DNA polymerase can be thermostable or mesophilic. Advantageously, a mesophilic DNA polymerase is used provided with a strand displacing activity, such as for example the Kleenow fragment of the DNA polymerase I of *E. coli*. The adding of this DNA dependent DNA polymerase is carried out at the beginning of the reaction and after the two first steps of heating necessary for the denaturation of the DNA beforehand at the implementation of the isothermic amplification.

Step (a) of the method of the invention consists: of heating the reaction mixture above in a manner to separate the DNA strands then of cooling in order to permit the hybridization of the primers, and of being placed at the temperature suitable for elongation by DNA polymerase. These steps of heating, of hybridization and of elongation are repeated a second time before obtaining a single-stranded target sequence whose ends are composed of reversed repeated sequences. This recombinant nucleic acid molecule has, at the same time, a role as a matrix and as a primer thanks to the hairpin structure at each one of its ends. Contrary to what is known with PCR, the amplification takes place here in a spontaneous fashion and at a constant temperature. The temperature is chosen in a manner permitting:

equilibrium of the reversed repeated sequences between the linear and hairpin forms.

The elongation of the primers by the DNA polymerase.

As shown in FIG. 3 attached, the amplification products rapidly attain a significant size, which can limit the elongation. The primers defining the size of the amplified fragment are chosen to optimize the amplification of the target sequence associated with a reporter gene.

A preferred operation of step (a) of isothermic amplification according to the invention is as follows:

i) heating a reaction mixture comprising the nucleic acid sample in which the target sequence is possibly present, the four triphosphate deoxynucleotides, salts and reactants assuring an optimal DNA polymerase activity, a DNA dependent DNA polymerase if it is thermophilic, (if not iii), a pair of primers specific for the target sequence to amplify and including the reverse repeated sequences, in a manner to separate the DNA strands, then ii) cooling it to permit hybridization of the primers, and iii) adding DNA polymerase if it is mesophilic, iv) placing the reaction mixture at a temperature suitable for the elongation by DNA polymerase.

v) repeating a second time the steps of heating (i), hybridization (ii) adding of the DNA polymerase if it is mesophilic (iii) and elongation (iv) in order to obtain a to target sequence whose ends are composed of reverse repeated sequences.

vi) letting the amplification reaction be carried out with the products of the previous step as matrix and primer, at a constant temperature chosen in a manner so as to permit:

equilibrium of the reverse repeated sequences between the linear and hairpin forms.

elongation of the primers by DNA dependent DNA polymerase.

Moreover, the amplification products can be specifically cut by a restriction enzyme, during or after the amplification reaction of the target sequence combined with the reporter gene of step (a). The restriction site is preferably situated at the level of one of the primers and more preferably in a loop of a hairpin, more precisely in two reverse repeated sequences of one of the primers.

The choice of the primers and of the cutting site of the enzyme will be defined for an effective transcription of the reporter gene, in such a way that this cutting does not alter the later transcription of the reporter gene.

In the case of the pair of preferred primers A described previously, the cutting site can be situated on the two primers and thus be identical or different on each of the primers.

The invention therefore equally has for an object a set of primers as defined above capable of being used in the previous method characterized in that at least one of the two primers comprises a restriction site. If the two primers possess a restriction site, they can be identical or different.

Preferably, the restrict site present on at least one of the primers is situated in a loop of a hairpin, more precisely between two repeated reverse sequences of one of the primers.

The invention also relates to the reaction mixture for the carrying out of the isothermic amplification method of the invention above comprising the four triphosphate deoxynucleotides, salts and reactants assuring an optimal activity of the DNA polymerase, a DNA dependent DNA polymerase, a pair of primers specific for the target sequence to amplify and comprising at 5' the reverse repeated sequences containing the reporter sequences.

The invention also relates to a kit for the implementation of the method of detection of a target sequence in a DNA sample comprising a set of primers as defined above, an amplification reaction mixture, optionally one or several restriction enzymes, a DNA dependent RNA polymerase, a DNA dependent DNA polymerase, the mixtures necessary for the transcription, for the translation and for the revelation of the reporter molecule.

Outside of the specific examples of the kit previously described where the target substance is a target nucleic acid sequence, the invention relates to kits for the implementation of the method of the invention, regardless of the target substance, such a kit is characterized in that it comprises at least a reporter gene, the mixtures necessary for transcription, for translation and for the revelation of the protein encoded by the reporter gene.

It is also possible to combine in a single tube several detections according to the method of the invention. In this case, different reporters are used to detect each of the target substances.

It is also possible to use the same reporter for several target substances. A positive result thus uniquely indicates the presence of one or the other of the target substances.

The transcription and translation reaction (step b) can be broken down into two distinct steps or simultaneous. In the latter case, the transcription and translation reactions are carried out simultaneously. On the other hand, the breaking down of the steps permits an easier optimization of the yields of each step, and thus produces more significant quantities of the reporter protein, which is especially useful in the case of enzymes of low specific activity.

The separation between the transcription and translation also permits avoiding the problems of degradation of the DNA matrix by the nucleases if they were prepared by PCR. In effect, the constituents of the transcription are slightly contaminated by nucleases, contrary to the translation extracts.

Moreover, the use of different cellular translation extracts according to the origin of the reporter gene permits optimization of the translation. In effect, the phase of translation of the transcript of step (b) is advantageously carried out with a cellular extract of the same origin or of an origin close to that of the reporter gene. There can be cited by way of example the use of a translation extract prepared starting from eukaryotic cells for the translation of a eukaryotic reporter gene. In another illustrative case, the translation extract is prepared starting from extremophilic organisms for the translation of a reporter gene from the same organism or from another extremophilic organism of the same type (thermophiles, halophiles, acidophiles, etc . . . ).

These specific extracts permit an increase in the effectiveness of the translation. But they can also be carried out with a standard extract such as for example an *E. coli* extract.

The process of the invention is thus notable in that it makes use of an adequacy between the expression punctuation of the transcripts and the translation extracts used. These extracts are also characterized in that either they do not contain the sought-after property, or they contain it but it is not detectable in the conditions of the test carried out for detecting the sought-after function. It relates for example to the use of a translation extract containing a mesophilic beta-galactosidase activity permitting translation of an mRNA of a thermophilic beta-galactosidase and the detection of the activity of this latter at high temperature, which eliminates the mesophilic beta-galactosidase activity.

A particular embodiment of the process of the invention consists of using at step (b) a translation extract which is in fact a mixture of several translation extracts. It can also relate for example to a translation extract of *E coli* overexpressing a chaperon protein A mixed with a translation extract of *E. coli* overexpressing a chaperon protein B. Any type of mixture is contemplated so long as it corresponds to the characteristics described above. In the same manner, it is possible to use a translation extract in which are added one or several specific tRNAs of one or several codons. The translation extracts thus obtained thereby permit translation of the mRNA comprising these specific codons, such as for example the translation of an mRNA containing an amber codon by adding in the translation extract a suppressor tRNA.

The treatment of step (b) with a translation extract can also be carried out with a standard translation extract whether it be one originating from the sample as for example an extract of *E coli* and/or any other cellular extract(s) supplemented or not by molecules of interest such as those, for example, indicated previously (tRNA, chaperon . . . ).

It is equally possible to add to the translation extract of step (b) one or several substances favoring a refolding or a more effective maturation of the expressed proteins, such as for example chaperons, detergents, sulfobetaines, membrane extracts, etc . . .

According to a particular embodiment of step (c), the revelation of the activity of the protein encoded by the reporter gene, also designated "reporter molecule" is carried out by contacting the reporter molecule with one or several substrates capable of revealing its activity.

Any type of specific substrate can be contemplated by a person skilled in the art in order to highlight the presence of the activity of the protein encoded by the reporter gene. A person skilled in the art will be able for example to refer to works such as Methods In Enzymology or Annual Review of Biochemistry, in which a large number of methods of mixture of enzymes and of preparation of substrate have been described.

The measurement of the activity of the protein of step (c) can be read directly in a fluorimeter reader if the reporter is for example GFP or by a calorimeter if the reporter is for example betalactamase. The readers are adapted for the revelation of the reporter. One can equally contemplate measurements by absorbance, viscosity, mass spectrophotometry etc . . . It can also be contemplated to carry out a reading continuously of the reporter activity, if the latter lends itself to it.

A particular application of the process of the invention consists of administrating the target substance labeled by the reporter gene and the sequences necessary for its expression, for example to an organisms or in a process, then searching for, by the pursuit of the steps of the invention up to step (c) of the method of the invention, in a sample withdrawn from said organism or from said process, the protein encoded by said reporter gene.

The method of the invention can also advantageously be automated, notably if the number of samples to analyze is high. The samples containing the target substances are thus placed on a support which can correspond to biochips or microtitration plaques which can contain several dozens to several thousands of sites. These supports are placed on an automatic machine for:

the preparation of the target substances (step a), the adding of the transcription and translation reactants (step b). The revelation of the reporter molecule (step c).

Consequently, the invention relates to a device comprising an arrangement of one or several supports, of robots and of a reader of said supports for the carrying out of the steps of the method described previously.

The invention equally concerns a process of labeling a substance corresponding to step (a) of the method of the invention described above. There invention therefore also concerns a substance labeled by a reporter gene and the elements necessary for the in vitro expression of said reporter gene capable of being obtained by this labeling process.

The invention finally concerns the use of a reporter gene and the elements necessary for the in vitro expression of said reporter gene as a label of a target sequence.

Other advantages and features of the invention will appear form the examples of carrying out the invention which follow.

EXAMPLE I

Labeling by PCR and Detection

1) The gene coding for microperoxidase 8 (MP8) was cloned in the expression vector pET26b+.

For this, two partially complementary oligonucleotides MICRO1 and MICRO2 were hybridized thus producing a double-stranded DNA fragment with compatible protruding ends respectively with a restriction site NdeI at the ATG side of the gene and with a site XhoI at the other end. This DNA fragment was inserted in the vector pET26b+ digested by NdeI and XhoI. In this way, the obtained plasmid contains the gene coding for the MP8 under the control of the promoter of the T7 RNA polymerase and its terminator situated on both sides.

Sequence MICRO1: 5' TATGTGCGCACAATGTCATA-CAGTAGAATAATAAC (SEQ ID NO:1)

Sequence MICRO2: 5' TCGAGTTATTATTCTACTG-TATGACAATTGTGCGCACA (SEQ ID NO:2)

Double-stranded DNA fragment:

```
Compatible                                    Compatible
NdeI                                          XhoI
5' TATG TGC GCA CAA TGT CAT ACA GTA GAA TAA TAA C      (SEQ ID NO:1)

3' AC ACG CGT GTT ACA GTA TGT CAT CTT ATT ATT CAGCT    (SEQ ID NO:3)
   Met Cys Ala Gln Cys His Thr Val Glu Stop Stop
```

2) This plasmid then served as matrix during the following PCR:

plasmid: about 100 ng
pET5' primer: 10 pmol
pET3' primer: 10 pmol
Taqpol (Appligene): 2 U
DNTP: 2001 µM each
Mix Taqpol Appligene: 1×
pET5' AGATCTCGATCCCGCGAAATTAATACG (SEQ ID NO:4)
pET3' CAAAAAACCCCTCAAGACCCGTTTAG (SEQ ID NO:5)

The amplification cycles carried out are the following: 3 mn at 94°, (30 s at 94°, 30 s at 60°, 1 mn at 72°) 30 times, 3 mn at 72°

This PCR permits amplification of a fragment containing, from 5' to 3', the promoter of the T7 RNA polymerase, the ribosome binding site, the MP8 gene and the transcription terminator of the T7 RNA polymerase. The PCR product was purified by phenol chloroform extraction and precipitated with ethanol.

3) The product of the PCT reaction was transcribed under the following conditions:
PCR product: 100 µg
T7RNA polymerase (NEB): 300U
T7 RNA polymerase mix (NEB): 1×
MgCl$_2$: 20 mM
NTP: 2 mM each
3 h at 37°

4) Some translations were carried out starting from 0, 2.75 and 11 µg of RNA under the following conditions:
43.8 µg of translation extract
0, 2.75 and 11 µg of RNA (0, 2.75, 11 µg of RNA)
water qsp 60 µl
3 h at 37°

5) The measuring of the microenzyme activity was carried out according to the following protocol described by Hirayama et al. Two standard ranges were carried out: one in the presence of 10 µl of translation control (without RNA) for the points where 10 µl of translation are measured. The results obtained are reported in the table below, expressed in units of luminescence.

TABLE 1

| Sample | 10 µl of translation |
|---|---|
| 0 (standard) | 1760 |
| 0.1 ng purified MP8 | 2368 |
| 1 ng purified MP8 | 5248 |
| 10 ng purified MP8 | 49088 |
| 100 ng purified MP8 | 1530144 |
| Translation with 2.75 µg of RNA | 2784 |
| Translation with 11 µg of RNA | 6752 |

The standard range obtained permits estimation of the quantity of MP8 produced at 0.14 ng with a translation of 2.75 µg showing that the PCR product can be demonstrated by the method which is the object of the invention.

EXAMPLE II

Detection of a Target DNA by Padlock, and Rolling Circle

1) The following oligonucleotide was prepared:

```
5'P.TTCAGCAGGATTCCCCACAGCAAAATTATTTCTAGAGGGAAACCGTTGTGGTCTCC
     homologous to the target   Complementary promoter strand T7

CTATAGTGAGTCGTATTAATTTTTATTATTCTACTGTATGACATTGTGCGCACATATGTA
                                   Complementary strand of the MP8 gene TATCTCCTTCTTAAAGTTAAACCCGTCGATCATAAGGCTTGG 3' (SEQ ID NO:6)
    Complementary        Homologous to the target
    Strand of the rbs
```

2) The plasmid used as target contains the following sequence: CTGTGGGGAATCCTGCTGAACCAAGCCTTATGATCGACGG (SEQ ID NO:7)

This sequence is recognized by the padlock probe above.

3) The ligation reaction is carried out as follows:
Linearized target plasmid: 2 µg
Ampligase mix (Epicenter): 1×
Ampligase: 10 U
Padlock oligo: 0.2 pmol
Water qsp: 50 µl The following temperature cycles are then carried out: 3 mn at 94°, (10 s at 94°, 10 s at 55°, 1 mn30 at 65°) 30 times.

4) The rolling circle amplification was done according to the following protocol:
ligation reaction: 10 µl
PADRCMP8 oligo: 10 pmol
DNTP: 384 µM
Klenow polymerase: 5 U
Water qsp 25 µl
2 h at 37.

The PADRCMP8 oligonucleotide has the following sequence: TTTAACTTTAAGAAGGAGATATAC (SEQ ID NO:8). It is complementary to a part of the padlock probe and therefore serves as a primer to the rolling circle.

5) Synthesis of the complementary strand 50 pmol of PADPCR5' oligonucleotide was added as 5 nmol of dNTP. This oligonucleotide is complementary to the strand amplified by rolling circle. The reaction mixture was heated 5 nm at 100° C. then allowed to cool in order to permit the hybridization of the oligonucleotide by the rolling circle.

5U of Klenow DNA polymerase and 5U of restriction enzyme AseI were then added. After incubation 2 h at 37°, double-stranded DNA molecules were obtained. An AseI site being present just upstream of the promoter sequence, the cutting by AseI permits shortening the multimers and thus will favor transcription.

The oligonucleotide PADPCR5' has the following sequence: 5' TTCAGCAGGATTCCCCACAG (SEQ ID NO:9)

6) Transcription

The transcription of the amplification product was carried out under the following conditions:

Above reaction product: 10 μl

T7 RNA polymerase (NEB): 150 U

T7 RNA polymerase mix (NEB): 1×

$MgCl_2$: 2 mM

DTT: 20 mM

NTP: 2 mM each 12 h at 37°

7) Translation: The translation was carried out as described in the previous example.

8) Measuring: The measuring of the activity of the microenzyme was carried out with 10 μl of translation according to the following protocol described by Hirayama et al. (Hirayama 0 et al., 1997, Analytical Biochem., 247, p 237–241): The negative standard is a complete experiment where the target plasmid was replaced by water at step 3. The translation and the measuring were done twice with different reaction mixes.

The results obtained are reported in Table 2 below expressed in units of luminescence.

TABLE 2

| Sample | Experiment 1 | Experiment 2 |
|---|---|---|
| Standard | 280213 | 179333 |
| positive | 396000 | 268207 |

BIBLIOGRAPHIC REFERENCE

1) Landegren, U., Samiotaki, M., Nilsson, M., Malmgren, H. and Kwiatkowski, M. (1996). Detecting genes with ligases. METHODS: A Companion to Methods in Enzymology 9, 84–90.
2) Landegren, U. and Nilsson M. (1997). Locked on target: strategies for future gene diagnostics. Ann. Med. 29, 585–590.
3) Nilsson M., Malmgren, H., Samiotaki, Kwiatkowski, M. Chowdhary, B. P. and Landegren, U. (1994). Padlock Probes: Circularizing oligonucleotides for localized DNA detection. Science 265, 2085–2088.
4) Nilsson M., Krejc, K., Koch, J., Kwiatkowski, M I, Gustavsson, P. and Landegren, U. (1997). Padlock probes reveal single-nucleotide differences, parent of origin and in situ distribution of centromeric sequences in human chromosomes 13 and 21. Nature Genetics 16, 252–255.

What is claimed is:

1. A method of detecting a target substance in a sample, comprising the following stages:
   (a) specifically labeling said target substance with a reporter gene and with the sequences necessary for in vitro expression of said reporter gene,
   (b) transcribing and translating, in vitro, said reporter gene to yield a reporter protein,
   (c) detecting, in vitro, the activity of said reporter protein encoded by said reporter gene, whereby reporter protein activity is indicative of the presence of said target substance in said sample,
   wherein, when said target substance is a nucleic acid sequence, the labeling step involves an acellular amplification and transcription and translation of said reporter gene does not yield a reporter protein which is a fusion protein with the protein encoded by the nucleic acid target.

2. The method of claim 1, wherein, when said target substance is a nucleic acid sequence, in vitro detection of said reporter gene does not utilize a protein encoded by a nucleic acid target.

3. The method of claim 1, wherein stage (b) comprises amplification of the transcripts prior to the translating at stage (b).

4. The method of claim 1, wherein the target substance at stage (a) is directly combined with the reporter gene and with the sequences necessary for in vitro expression of said reporter.

5. The method of claim 1, wherein the target substance at stage (a) is combined with the reporter gene and with the sequences necessary for reporter gene in vitro expression, wherein the target substance is combined by using a ligand specific for the target substance, said ligand being labeled with the reporter gene and with the sequences necessary for the in vitro expression of said reporter gene.

6. The method of claim 1, wherein the method further comprises the following stages:
   a') preparing a recombinant nucleic acid molecule comprising an RNA polymerase promoter, a reporter gene, an RNA polymerase terminator, or a combination thereof, said step of preparing starting from the sample, said recombinant nucleic acid molecule being in the 5' to 3' sense, said reporter gene possessing sequences necessary for reporter gene expression, wherein a target nucleic acid sequence is localized between any two members of the group consisting of the RNA polymerase promoter, the reporter gene, and the RNA polymerase terminator;
   b') transcribing and translating the products obtained at stage (a'); and
   c') identifying the activity of the protein encoded by the reporter gene, designated the reporter molecule, obtained at stage (b').

7. The method of claim 6, wherein the preparing of the nucleic acid molecule at stage (a') further comprises in vitro amplification of the target nucleic acid sequence.

8. The method of claim 7, wherein stage (a') further comprises amplification with the aid of two printers, said two primers comprising a sense primer with at least one part homologous to the 5' region of the target sequence, an anti-sense primer with at least one part homologous to the 3' region of the target sequence, said primers permitting expression of the reporter gene, said expression occurring after amplification of the target nucleic acid sequence and after stage (b).

9. The method of claim 7, wherein stage (a) further comprises the following stages:
   $a_1$) amplifying the target sequence with a sense primer and an anti-sense primer, said sense primer possessing an RNA polymerase promoter, said anti-sense primer possessing a 5' region homologous to the beginning of the sequence of the reporter gene,
   $a_2$) combining the product of stage ($a_1$) with the reporter gene to hybridize the amplified target sequence with the reporter gene, said reporter gene comprising an RNA polymerase terminator for its transcription, a translation regulation sequence for its translation, or a combination thereof; and
   $a_3$) amplifying the product of stage ($a_2$) with a sense primer and an anti-sense primer, wherein the sense primer is similar to that of stage ($a_1$) and the anti-sense primer comprises a part homologous to a region downstream of the reporter gene.

10. The method of claim 7, wherein stage (a) further comprises the following stages:
    a") amplifying the target sequence with a sense primer and an anti-sense primer, said sense primer possessing an RNA polymerase promoter, said anti-sense primer possessing a 5' region homologous to the beginning of the sequence of the reporter gene, and
    a'") amplifying the product of stage (a") with a sense primer and an anti-sense primer, wherein the sense primer is identical to that of stage (a") and the anti-sense primer is a mega-primer composed of a reporter gene and a translation regulation sequence.

11. The method of claim 7, wherein stage (a') further comprises an amplification reaction of the target sequence with a sense primer and an anti-sense primer wherein the sense primer possesses an RNA polymerase promoter and the anti-sense primer possesses a 5' region comprising a sequence coding for a translation regulation sequence, a reporter gene, a transcription terminator, or a combination thereof.

12. The method of claim 7, wherein the preparing of the nucleic acid molecule at stage (a') further comprises hybridization and ligation of a Padlock type probe with the target sequence.

13. The method of claim 12, wherein said probe is composed from 3' to 5' of segments separated by a complementary sequence of a reporter gene and the complementary sequence of a translation regulation sequence for its in vitro translation, said reporter gene possessing sequences complementary to a promoter.

14. The method of claim 12, wherein said probe is composed, from 5' to 3', of segments separated from 5' to 3' by an RNA polymerase promoter sequence, a translation regulation sequence and the sequence of a reporter gene.

15. The method of claim 12, wherein stage (b) comprises transcription of the reporter gene on the Padlock probe is carried out directly after its circularization and the synthesis of the complementary strand with the aid of a primer complementary to the padlock probe complementary to the target.

16. The method of claim 12, wherein, after circularization, the probe is used as a matrix for its replication by rolling circle.

17. The method of claim 16, wherein the rolling circle replication is carried out with the aid of a primer complementary to the padlock probe complementary to the target in order to initiate the replication by DNA polymerase, in such a fashion to produce a DNA matrix possessing a linking of reporter genes with all the signals necessary for its expression in vitro, and in that the complementary strand of this DNA matrix is synthesized starting with a second oligonucleotide primer so as to make this matrix double-stranded.

18. The method of claim 7, wherein the target nucleic acid sequence is isolated from the sample at stage (a) by specific isothermic amplification, said target nucleic acid sequence being isolated with the aid of a DNA dependent DNA polymerase and two specific primers of the target sequence, wherein the specific primers comprise a 3' part which can be specifically hybridized to the target sequence and a 5' part comprising at least one reverse repeat sequence for forming at a suitable temperature a so called hairpin structure.

19. The method of claim 18, wherein the two primers possess an inverted repeat sequence in order to form at a suitable temperature a hairpin structure, said inverted repeat sequences of the two primers capable of being identical or different.

20. The method of claim 18, wherein the isothermic amplification at stage (a) further comprises the following stages:
  (i) heating a reaction mixture, said mixture comprising the nucleic acid sample, four triphosphate deoxynucleotides, salts, reactants, a pair of primers, said salts and reactants being adapted to assure an optimal activity of the DNA polymerase, said pair of primers being specific for the target sequence to amplify and to separate the DNA strands, said pair of primers comprising the reverse repeat sequences, wherein if the DNA polymerase is thermostable then the mixture further comprises the DNA dependent DNA polymerase;
  (ii) cooling to permit the hybridization of the primer;
  (iii) adding the DNA polymerase if the DNA polymerase is not thermostable;
  (iv) placing the reaction mixture at sufficient temperature for elongation by DNA polymerase;
  (v) repeating stages (i), (ii), (iii), and (iv) in order to obtain a target sequence wherein the ends are composed of reverse repeat sequences; and
  (vi) amplifying products of stage (v), said amplifying occurring at a constant temperature, said temperature allowing the equilibrium of the repeat reverse sequences between the linear form and the hairpin form, said temperature allowing the elongation of the primers by DNA dependent DNA polymerase.

21. The method of claim 18, wherein products of the specific isothermic amplification can be specifically cut by a restriction enzyme, during or after the amplification of the target sequence.

22. A method of detecting at least one target substance in a sample comprising labeling said target substance with a reporter gene and expressing said reporter gene using in vitro expression,
  whereby expression of said reporter gene is indicative of the presence of said target substance in said sample, and
  wherein, when said at least one target substance is a nucleic acid sequence, the labeling step involves an acellular amplification and transcription and translation of said reporter gene does not yield a reporter protein which is a fusion protein with the protein encoded by the nucleic acid target.

23. The method of claim 22, wherein, when said target substance is a nucleic acid sequence, transcription and translation of said reporter gene does not yield a reporter protein which is a fusion protein with the protein encoded by a nucleic acid target.

24. The method of claim 22, wherein, when said target substance is a nucleic acid sequence, in vitro detection of said reporter gene does not utilize a protein encoded by a nucleic acid target.

25. A process for labeling a target substance comprising specifically labeling said target substance with a reporter gene and with the sequences necessary for in vitro expression of said reporter gene, wherein when said target substance is a nucleic acid sequence, the labeling step involves an acellular amplification.

26. The method of claim 1, wherein the presence of said target substance is necessary for detection of said reporter protein.

27. The method of claim 26, wherein said target substance is a nucleic acid sequence.

28. A method of diagnosing a condition associated with the presence of a target substance in a sample, comprising the following stages:
  (a) specifically labeling said target substance with a reporter gene and with the sequences necessary for in vitro expression of said reporter gene,
  (b) transcribing and translating, in vitro, said reporter gene to yield a reporter protein, and
  (c) detecting, in vitro, the activity of said reporter protein encoded by said reporter gene, whereby reporter protein activity is indicative of the presence of said target substance in said sample, and wherein, when said target substance is a nucleic acid sequence, the labeling step involves an acellular amplification and transcription and translation of said reporter gene does not yield a reporter protein which is a fusion protein with the protein encoded by the nucleic acid target; and
  (d) diagnosing the condition based on the presence or absence of said target substance.

29. The method of claim 28, wherein said condition is viral in origin.

30. The method of claim 28, wherein said condition is bacterial in origin.

31. The method of claim 28, wherein said condition is a genetic disease or cellular cancer.

* * * * *